United States Patent
Minamisawa et al.

(10) Patent No.: US 7,687,609 B2
(45) Date of Patent: Mar. 30, 2010

(54) GALECTIN-GLYCOSAMINOGLYCAN COMPLEX AND METHOD FOR CONTROLLING GALECTIN ACTIVITY

(75) Inventors: Toshikazu Minamisawa, Tokyo (JP); Kiyoshi Suzuki, Tokyo (JP); Jun Hirabayashi, Ibaraki (JP)

(73) Assignees: National Institute of Advanced Industrial Science and Technology, Tokyo (JP); Seikagaku Corporation, Tokyo (JP)

( * ) Notice: Subject to any disclaimer, the term of this patent is extended or adjusted under 35 U.S.C. 154(b) by 86 days.

(21) Appl. No.: 11/751,106

(22) Filed: May 21, 2007

(65) Prior Publication Data
US 2007/0269833 A1    Nov. 22, 2007

(30) Foreign Application Priority Data
May 19, 2006    (JP)    ............... 2006-140600

(51) Int. Cl.
*C07K 14/42*    (2006.01)
*A61K 38/00*    (2006.01)

(52) U.S. Cl. ............... 530/396; 530/395; 530/322; 530/387.5; 514/8; 514/9; 514/42; 514/23

(58) Field of Classification Search ............ None
See application file for complete search history.

(56) References Cited

U.S. PATENT DOCUMENTS

2004/0023855 A1 *    2/2004    John et al. ............... 514/8

OTHER PUBLICATIONS

Wikipedia (2009, updated) Chondroitin sulfate, http://en.wikipedia.org/wiki/Chondroitin_sulfate, pp. 1-8.*
Alkhalil et al. (2000) Structural requirements for the adherence of Plasmodium falciparum-infected erythrocytes to chondroitin sulfate proteoglycans of human placenta, J. Biol. Chem., vol. 275, No. 51, pp. 40357-40364.*
Ahmad et al. (2004) Thermodynamic binding studies of bivalent oligosaccharides to galectin-1, galectin-3, and the carbohydrate recognition domain of galectin-3, Glycobiology, vol. 14, No. 9, pp. 817-825.*

* cited by examiner

*Primary Examiner*—Anand U Desai
*Assistant Examiner*—Samuel Liu
(74) *Attorney, Agent, or Firm*—Sughrue Mion, PLLC

(57) ABSTRACT

A complex consisting of galectin-3 and chondroitin oligosaccharide and methods for seperating and detecting the chondroitin oligosaccharide in a sample using the immobilized complex.

4 Claims, No Drawings

GALECTIN-GLYCOSAMINOGLYCAN COMPLEX AND METHOD FOR CONTROLLING GALECTIN ACTIVITY

BACKGROUND OF THE INVENTION

1. Field of the Invention

The present invention relates to a galectin-glycosaminoglycan complex and a method for controlling galectin activity.

2. Brief Description of the Background Art

The following abbreviations are used in this specification.
Gal: Galactose residue:
GlcNAc: N-Acetylglucosamine residue
NeuAc: N-Acetylneuraminic acid residue
GalNAc: N-Acetylgalactosamine residue
GlcA Glucuronic acid residue
6S: Sulfate group retained at the C6 position
α2-3: α2-3 Glycosidic linkage
β1-4: β1-4 Glycosidic linkage
β1-3: β1-3 Glycosidic linkage Galectin is a general name for an animal lectin family proposed in 1992 (Barondes, S. H. et al., *Cell*, 76, 597-598 (1994)). Galectin are required to have binding specificity for β-linked galactose residue (hereinafter sometimes referred to as "β-galactoside") and to have an amino acid primary sequence which characterizes the galectin family. As mammalian galectins, it has been proposed to call them by adding numbers in order of discovery (in order of register to GenBank). In accordance with this system, galectins 1 to 15 (kinds) have so far been found in mammals, and it is considered that they have their physiological functions in the living bodies by binding to various galactose-containing carbohydrates. Respective kinds of galectin have slightly different binding (recognizing) specificities for various galactose-containing oligosaccharide chains.

A total of 12 kinds of human-derived galectin families have so far been identified (Douglas N. W. Cooper, *Biochimica et Biophysica Acta*, 1572, 209-231 (2002)). That is, they are galectin-1 to 4 (Gal-1 to 4), galectin-7 to 10 (Gal-7 to 10) and galectin-12 (Gal-12). The members constituting this family are further divided into 3 subtypes based on their structures (Hirabayashi, J. et al., *Glycobiology*, 3, 297-304 (1993)).

Each of galectin-1, -2, -7 and -10 has a single carbohydrate recognizing region (carbohydrate-recognition domain; CRD) consisting of approximately from 130 to 140 amino acid residues, and belongs to the prototype. Galectin-3 has an amino-terminal domain, a type which is different from the carboxy-terminal CRD, and is the only one chimeric type. Each of galectin-4, -8, -9 and -12 has two CRDs connected via a linker peptide and is classified into a tandem repeat type.

Each of the prototype and chimeric type galectins has one CRD, and galectin-1, -2 and -3, and probably galactin-7 and -10 too, among them form a dimmer/multimer (polymer) and have a multivalent binding function, so that it is considered that they have a function to crosslink a complex carbohydrate (glycoconjugate).

Glycosaminoglycan is the carbohydrate moiety of proteoglycan among representative glycoconjugates (glycoprotein, glycolipid and proteoglycan) which are present as an extracellular matrix component and the like in the living bodies (JP-A-4-80201, JP-A-4-80202, JP-A-9-30979, JP-A-5-236951). About 10 kinds such as hyaluronic acid, chondroitin sulfate, keratan sulfate and the like are known as the glycosaminoglycan, and they have a characteristic common structure, namely an alternate repeating structure of N-acetyl-hexosamine and uronic acid (or galactose).

Frontal affinity chromatography (hereinafter sometimes referred to as FAC) is known as a method which can determine affinity between a biomaterial such as an enzyme or lectin and a substrate analog or oligosaccharide chain with high sensitivity and high accuracy.

FAC is a technique of affinity chromatography using liquid chromatography. In the FAC, in general, a column to which a certain molecule was immobilized is prepared, and a molecule to be interacted therewith is labeled with a fluorescent material and flowed as the solvent. When the elution front end (front) observed by a fluorescence detector is delayed than the case of unbinding molecule, the intermolecular affinity is determined by using the fact that degree of the delay is proportional to the intermolecular affinity (*Seikagaku*, 76(3), 256-268 (2004)).

In JP-A-2004-215612 and JP-A-2003-189874, binding of galectin to carbohydrates which are found in the "glycoprotein" and "glycolipid" among glycoconjugates is analyzed by making use of the FAC techniques, by eluting fluorescence-labeled carbohydrates through a galectin-immobilized column.

SUMMARY OF THE INVENTION

The present invention provides novel complexes of various galectin molecules with various glycosaminoglycan molecules (hereinafter sometimes referred to as "galectin -glycosaminoglycan complex"). In addition, although it has been considered that galectin molecules recognize only β-galactoside, the present invention also provides novel galectin -glycosaminoglycan complexes without β-galactoside.

According to the present invention, a galectin-glycosaminoglycan complex is provided as a novel substance, and also a glycosaminoglycan molecule-immobilized carrier as a tool for separating, purifying or measuring the conjugate or the galectin molecule constituting the complex, and a galectin molecule-immobilized carrier as a tool for the detailed structural-based separation, purification or measurement of the complex or the glycosaminoglycan molecule constituting the complex, are provided.

In addition, since there is a possibility that the physiological function of galectin molecules in the living body can be controlled in both of the positive and negative directions by the glycosaminoglycan molecules applied from the outside, application of these galectin molecule glycosaminoglycan molecules to medical treatments are expected. Particularly, an agent for controlling the activity of a galectin molecule, which comprises a glycosaminoglycan molecule, and a method for controlling the same are provided.

DETAILED DESCRIPTION OF THE INVENTION

Using FAC, the present inventors have conducted a comprehensive analysis of the interactions between various galectin molecules (galectin-1, 3, 8N, 8C, 9N and 9C; N and C respectively represent N-terminal side carbohydrate-recognition domain and C-terminal side carbohydrate-recognition domain)-immobilized columns and various fluorescence-labeled glycosaminoglycan molecules. As a result, novel affinity was found by the combination of specific galectin molecules and glycosaminoglycan molecules to thereby accomplish the present invention.

Specifically, the present invention relates to the following (1) to (18).

(1) A complex between a galectin molecule represented by the following (I) and a glycosaminoglycan molecule represented by the following (II):

(I) galectin-1 (Gal-1) or C-terminal carbohydrate-recognizing domain (CRD) of galectin-9 (Gal-9C);
(II) a carbohydrate which has a repeating structure of Gal-GlcNAc and has a non-sulfated β-galactoside at its non-reducing terminal,
wherein Gal represents a galactose residue, and GlcNAc represents an N-acetylglucosamine residue.

(2) The complex according to the above item (1), wherein the galectin molecule is galectin-1, and the glycosaminoglycan molecule is any one of the following (i) and (ii):
(i) a cornea type keratan sulfate (keratan sulfate-I: KS-I);
(ii) an oligosaccharide chain having any one of structures represented by the following formulae (1) to (3):

G2K1: Gal β1-4 GlcNAc β1-3 Gal    (1)

L2L2: Gal β1-4 GlcNAc6S β1-3 Gal β1-4 GlcNAc6S    (2)

L2L4: Gal β1-4 GlcNAc6S β1-3 Gal6S β1-4 GlcNAc6S    (3), wherein Gal represents a galactose residue, GlcNAc represents an N-acetylglucosamine residue, 6S means that a sulfate group is retained at the C6 position, β1-4 represents a β1-4 glycosidic linkage, and β1-3 represents a β1-3 glycosidic linkage.

(3) The complex according to the above item (1), wherein the galectin molecule is galectin-9C, and the glycosaminoglycan molecule is any one of the following (i) and (ii):
(i) a cornea type keratan sulfate (keratan sulfate-I: KS-I) or a cartilage type keratan sulfate (keratan sulfate-II: KS-II);
(ii) an oligosaccharide chain having any one of structures represented by the following formulae (1) to (4):

G2K1: Gal β1-4 GlcNAc β1-3 Gal    (1)

L2L2: Gal β1-4 GlcNAc6S β1-3 Gal β1-4 GlcNAc6S    (2)

L2L4: Gal β1-4 GlcNAc6S β1-3 Gal6S β1-4 GlcNAc6S    (3)

G1L1: GlcNAc β1-3 Gal β1-4 GlcNAc    (4)

wherein Gal represents a galactose residue, GlcNAc represents an N-acetylglucosamine residue, 6S means that a sulfate group is retained at the C6 position, β1-4 represents a β1-4 glycosidic linkage, and β1-3 represents a β1-3 glycosidic linkage.

(4) A complex between a galectin molecule represented by the following (I) and a glycosaminoglycan molecule represented by the following (II):
(I) N-terminal carbohydrate-recognizing domain of galectin-8 (galectin-8N: Gal-8: Gal-8N);
(II) any one of the following (II-1) and (II-2):
(II-1) a carbohydrate having a non-sulfated N-acetylgalactosamine;
(II-2) a carbohydrate having a sialic acid residue at the non-reducing terminal.

(5) The complex according to the above item (4), wherein the glycosaminoglycan molecule is any one of the following (i) and (ii):
(i) dermatan (DN);
(II) an oligosaccharide chain having a structure represented by the following formula (5):

SL2L4: NeuAc α2-3 Gal β1-4 GlcNAc6S β1-3 Gal6S β1-4 GlcNAc6S    (5)

wherein NeuAc represents an N-acetylneuraminic acid residue (known as one of the sialic acids), Gal represents a galactose residue, GlcNAc represents an N-acetylglucosamine residue, 6S means that a sulfate group is retained at the C6 position, α2-3 represents α2-3 glycosidic linkage, β1-4 represents a β1-4 glycosidic linkage, and β1-3 represents a β1-3 glycosidic linkage.

(6) A complex of a galectin molecule represented by the following (I) and a glycosaminoglycan molecule represented by the following (II):
(I) galectin-3 (Gal-3) or N-terminal carbohydrate-recognizing domain of galectin-9 (galectin 9N: Gal-9N),
(II) any one of the following (II-1) and (II-2):
(II-1) a carbohydrate which has a repeating structure of Gal-GlcNAc and has a non-sulfated β-galactoside;
(II-2) a carbohydrate which has a non-sulfated N-acetylgalactosamine residue.

(7) The complex according to the above item (6), wherein the galectin molecule is galectin-3, and the glycosaminoglycan molecule is any one of the following (i) to (v):
(i) a cornea type keratan sulfate (keratan sulfate-I: KS-I) or a cartilage type keratan sulfate (keratan sulfate-II: KS-II);
(ii) an oligosaccharide chain having any one of structures represented by the following formulae (1) to (5):

G2K1: Gal β1-4 GlcNAc β1-3 Gal    (1)

L2L2: Gal β1-4 GlcNAc6S β1-3 Gal β1-4 GlcNAc6S    (2)

L2L4: Gal β1-4 GlcNAc6S β1-3 Gal6S β1-4 GlcNAc6S    (3)

G1L1: GlcNAc β1-3 Gal β1-4 GlcNAc    (4)

SL2L4: NeuAc α2-3 Gal β1-4 GlcNAc6S β1-3 Gal6S β1-4 GlcNAc6S    (5)

wherein NeuAc represents an N-acetylneuraminic acid residue, Gal represents a galactose residue, GlcNAc represents an N-acetylglucosamine residue, 6S means that a sulfate group is retained at the C6 position, α2-3 represents α2-3 glycosidic linkage, β1-4 represents a β1-4 glycosidic linkage, and β1-3 represents a β1-3 glycosidic linkage;
(iii) dermatan (DN);
(iv) chondroitin (CH);
(v) an oligosaccharide chain having any one of structures represented by the following formulae (6) to (12):

CH6: GlcA β1-3 (GalNAc β1-4 GlcA β1-3)$_2$ GalNAc    (6)

CH7: (GalNAc β1-4 GlcA β1-3)$_3$ GalNAc    (7)

CH8: GlcA β1-3 (GalNAc β1-4 GlcA β1-3)$_3$ GalNAc    (8)

CH9: (GalNAc β1-4 GlcA β1-3)$_4$ GalNAc    (9)

CH10: GlcA β1-3 (GalNAc β1-4 GlcA β1-3)$_4$ GalNAc    (10)

CH11: (GalNAc β1-4 GlcA β1-3)$_5$ GalNAc    (11)

CH12: GlcA β1-3 (GalNAc β1-4 GlcA β1-3)$_5$ GalNAc    (12)

wherein GlcNAc represents an N-acetylglucosamine residue, GalNAc represents an N-acetylgalactosamine residue, GlcA represents a glucuronic acid residue, β1-4 represents a β1-4 glycosidic linkage, and β1-3 represents a β1-3 glycosidic linkage.

(8) The complex according to the above item (6), wherein the galectin molecule is galectin-9N, and the glycosaminoglycan molecule is any one of the followings (i) to (v):
(i) a cornea type keratan sulfate (keratan sulfate-I: KS-I) or a cartilage type keratan sulfate (keratan sulfate-II: KS-II);

(ii) an oligosaccharide chain having any one of structures represented by the following formulae (1) to (4):

G2K1: Gal β1-4 GlcNAc β1-3 Gal (1)

L2L2: Gal β1-4 GlcNAc6S β1-3 Gal β1-4 GlcNAc6S (2)

L2L4: Gal β1-4 GlcNAc6S β1-3 Gal6S β1-4 GlcNAc6S (3)

G1L1: GlcNAc β1-3 Gal β1-4 GlcNAc (4)

wherein Gal represents a galactose residue, GlcNAc represents an N-acetylglucosamine residue, 6S means that a sulfate group is retained at the C6 position, β1-4 represents a β1-4 glycosidic linkage, and β1-3 represents a β1-3 glycosidic linkage,
(iii) dermatan (DN);
(iv) chondroitin (CH);
(v) an oligosaccharide chain having any one of structures represented by the following formulae (6) to (15):

CH6: GlcA β1-3 (GalNAc β1-4 GlcA β1-3)$_2$ GalNAc (6)

CH7: (GalNAc β1-4 GlcA β1-3)$_3$ GalNAc (7)

CH8: GlcA β1-3 (GalNAc β1-4 GlcA β1-3)$_3$ GalNAc (8)

CH9: (GalNAc β1-4 GlcA β1-3)$_4$ GalNAc (9)

CH10: GlcA β1-3 (GalNAc β1-4 GlcA β1-3)$_4$ GalNAc (10)

CH11: (GalNAc β1-4 GlcA β1-3)$_5$ GalNAc (11)

CH12: GlcA β1-3 (GalNAc β1-4 GlcA β1-3)$_5$ GalNAc (12)

CH3: GalNAc β1-4 GlcA β1-3 GalNAc (13)

CH4: GlcA β1-3 GalNAc β1-4 GlcA β1-3 GalNAc (14)

CH5: (GalNAc β1-4 GlcA β1-3)$_2$ GalNAc (15)

wherein GlcNAc represents an N-acetylglucosamine residue, GalNAc represents an N-acetylgalactosamine residue, GlcA represents a glucuronic acid residue, β1-4 represents a β1-4 glycosidic linkage, and β1-3 represents a β1-3 glycosidic linkage.
(9) A carrier on which the galectin molecule constituting the complex according to any one of the above items (1) to (8) is immobilized, which is useful for separating, purifying and/or detecting the complex or the glycosaminoglycan molecule constituting the complex.
(10) A carrier on which the glycosaminoglycan molecule constituting the complex according to any one of the above items (1) to (8) is immobilized, which is useful for separating, purifying and/or detecting the complex or the galectin molecule constituting the complex.
(11) A method for separating, purifying and/or detecting the complex according to any one of the above items (1) to (8) or the glycosaminoglycan molecule constituting the complex, which comprises using the carrier according to the above item (9).
(12) A method for separating, purifying and/or detecting the complex according to any one of the above items (1) to (8) or the galectin molecule constituting the complex, which comprises using the carrier according to the above item (10).
(13) A kit for separating, purifying and/or detecting the complex according to any one of the above items (1) to (8) or the galectin molecule constituting the complex, which comprises a carrier on which the glycosaminoglycan molecule constituting the complex is immobilized.
(14) A kit for separating, purifying and/or detecting the complex according to any one of the above items (1) to (8) or the glycosaminoglycan molecule constituting the complex, which comprises a carrier on which the galectin molecule constituting the complex is immobilized.
(15) A method for enhancing or inhibiting biological activity of the galectin molecule constituting the complex according to any one of (1) to (8), which comprises using the glycosaminoglycan molecule constituting the complex.
(16) A composition for enhancing or inhibiting biological activity of the galectin molecule constituting the complex according to any one of (1) to (8), which comprises the glycosaminoglycan molecule constituting the complex.
(17) A medical material which comprises the composition according to (16).
(18) A medical material which comprises the complex according to any one of (1) to (8).

Examples of the glycosaminoglycan molecule of the present invention include those which have structural characteristics of the following:
(1) a carbohydrate which has a repeating structure of Gal-GlcNAc and has a non-sulfated β-galactoside at its non-reducing terminal,
(2) a carbohydrate having a non-sulfated N-acetylgalactosamine residue (β-N-acetylgalactosaminide); and
(3) a carbohydrate having a sialic acid residue at the non-reducing terminal.

The structural characteristics described above (1) to (3) are also involved in high molecular weight glycosaminoglycan molecules which are present in the nature, and the production procedure of glycosaminoglycan molecules is not particularly limited, so that the glycosaminoglycan molecules used in the present invention may be those which are produced by organic or chemo-enzymatic synthesis. In addition, those which are commercially available can be used as the glycosaminoglycan molecules used in the present invention.

As the chondroitin (CH) and cornea type keratan sulfate (KS-I) used in the present invention, those which are broadly commercially available (manufactured by Seikagaku Corporation) can be used. Also, the cartilage type keratan sulfate (KS-II) can be prepared from shark cartilages by a conventionally known method. In addition, dermatan (DN) can be prepared by complete de-sulfation of dermatan sulfate (manufactured by Seikagaku Corporation) by a conventionally known chemical method.

(1) Carbohydrate which has a Repeating Structure of Gal-GlcNAc and has a Non-sulfated β-galactoside at its Non-reducing Terminal Regarding the carbohydrate used in the present invention which has a non-sulfated β-galactoside at the non-reducing terminal and has a repeating structure of Gal-GlcNAc, its molecular weight is not limited, so long as it has a non-sulfated β-galactoside at the non-reducing terminal. As such a glycosaminoglycan, keratan sulfate is preferable, and a cornea type keratan sulfate (keratan sulfate-I: KS-I) or a cartilage type keratan sulfate (keratan sulfate-II: KS-II) is more preferable.

As the carbohydrate used in the present invention which has a non-sulfated β-galactoside at the non-reducing terminal and has a repeating structure of Gal-GlcNAc, an oligosaccharide chain prepared by decreasing the molecular weight of keratan sulfate to an optional level by a chemical or biochemical means (hereinafter be referred to as "keratan sulfate-constituting oligosaccharide") may also be used. The keratan sulfate-constituting oligosaccharide used in the present invention can be prepared by the method described in JP-A-2006-047240.

TABLE 1

Keratan sulfate constituting oligosaccharides

| Abbreviation | Sequence |
|---|---|
| G2K1 | Gal β1-4 GlcNAc β1-3 Gal |
| G1L1 | GlcNAc β1-3 Gal β1-4 GlcNAc |
| G4L4 | GlcNAc6S β1-3 Gal6S β1-4 GlcNAc6S |
| L2L2 | Gal β1-4 GlcNAc6S β1-3 Gal β1-4 GlcNAc6S |
| L2L4 | Gal β1-4 GlcNAc6S β1-3 Gal6S β1-4 GlcNAc6S |
| L4L4 | Gal6S β1-4 GlcNAc6S β1-3 Gal6S β1-4 GlcNAc6S |
| SL2L4 | NeuAc α2-3 Gal β1-4 GlcNAc6S β1-3 Gal6S β1-4 GlcNAc6S |

In Table 1, Gal represents a galactose residue, GlcNAc represents an N-acetylglucosamine residue, 6S means that a sulfate group is retained at the C6 position, GalNAc represents an N-acetylgalactosamine residue, GlcA represents a glucuronic acid residue, and NeuAc represents an N-acetyl-neuraminic acid residue.

The keratan sulfate and the oligosaccharide chains shown in Table 1, all used in the present invention may be further structure-modified, so long as one or more non-sulfated β-galactoside are present in the structure. In addition, these may be used as a mixture or alone as a purified product. Examples of the above-described oligosaccharide chains having one or more non-sulfated β-galactoside in the structure include G2K1, G1L1, L2L2 and L2L4.

In Examples of the present invention, KS-I showed binding affinity to galectin-1, -3, -8N, -9N and -9C. Also, KS-II showed binding affinity to galectin-3, -9N and -9C. G2K1, L2L2 and L2L4 showed binding affinity to galectin-1, -3, -9N and -9C, and G1L1 showed binding affinity to galectin-3 and -9N.

(2) Carbohydrate having a Non-sulfated N-acetylgalactosamine Residue (β-N-acetylgalactosaminide)

Examples of the carbohydrate having a non-sulfated N-acetylgalactosamine residue (β-N-acetylgalactosaminide) include (2-1) dermatan and (2-2) chondroitin. The molecular weight of the carbohydrates used in the present invention having a non-sulfated N-acetylgalactosamine residue are not particularly limited, so long as they have one or more non-sulfated N-acetylgalactosamine residue, their molecular weight may be reduced by an optional method, and these may be modified derivatives thereof. These may be used as a mixture or as a purified product alone.

(2-1) Dermatan (DN)

Among members of dermatan sulfate (CSB), those which have a structure in which a non-sulfated N-acetylgalactosamine residue is present in its structure are preferable, those which have a structure in which sulfate groups on the non-sulfated N-acetylgalactosamine residues in the CSB structures are removed at an optional ratio are more preferable, and those which have an almost completely de-sulfated structure are particularly preferable.

In Examples of the present invention, dermatan showed binding affinity to galectin-3, -8N and -9N.

(2-2) Chondroitin (CH)

Among the members of chondroitin sulfate (e.g., CSA, CSC, CSD, CSE and the like), the chondroitin used in the present invention preferably has such a structure that a non-sulfated N-acetylgalactosamine residue is present in its structure and also such a structure that sulfate groups in the N-acetylgalactosamine residues in the chondroitin sulfate structures are removed at an optional ratio.

An oligosaccharide prepared by decreasing the molecular weight of chondroitin to an optional level by a chemical or biochemical means (hereinafter referred to as "chondroitin oligosaccharide") may also be used. Abbreviations and sequences of the chondroitin oligosaccharides used in the present invention are shown in Table 2. The chondroitin oligosaccharides used in the present invention can be prepared from chondroitin by the method described in PCT/JP2006/322847.

TABLE 2

Chondroitin oligosaccharides

| Abbreviations | Sequences |
|---|---|
| CH3 | GalNAc β1-4 GlcA β1-3 GalNAc |
| CH4 | GlcA β1-3 GalNAc β1-4 GlcA β1-3 GalNAc |
| CH5 | (GalNAc β1-4 GlcA β1-3)$_2$ GalNAc |
| CH6 | GlcA β1-3 (GalNAc β1-4 GlcA β1-3)$_2$ GalNAc |
| CH7 | (GalNAc β1-4 GlcA β1-3)$_3$ GalNAc |
| CH8 | GlcA β1-3 (GalNAc β1-4 GlcA β1-3)$_3$ GalNAc |
| CH9 | (GalNAc β1-4 GlcA β1-3)$_4$ GalNAc |
| CH10 | GlcA β1-3 (GalNAc β1-4 GlcA β1-3)$_4$ GalNAc |
| CH11 | (GalNAc β1-4 GlcA β1-3)$_5$ GalNAc |
| CH12 | GlcA β1-3 (GalNAc β1-4 GlcA β1-3)$_5$ GalNAc |

In Table 2, Gal represents a galactose residue, GlcNAc represents an N-acetylglucosamine residue, GalNAc represents an N-acetylgalactosamine residue and GlcA represents a glucuronic acid residue.

In Examples of the present invention, chondroitin and chondroitin oligosaccharides CH3 to CH12 showed a length-dependent binding affinity to galectin-3 and -9N, and showed particularly strong binding affinity to galectin-9N. In addition, galectin-3 was the binding affinity particularly hexasaccharide or more (CH6 to CH12) among the CH3 to CH12 prepared by decreasing the molecular weight.

(3) Carbohydrate having a Sialic Acid Residue at the Non-reducing Terminal

Preferred examples of the glycosaminoglycan carbohydrate used in the present invention having such a structure that a sialic acid residue is located at the non-reducing terminal include SL2L4 among the keratan sulfate constituting oligosaccharides shown in Table 1.

In Examples of the present invention, SL2L4 showed binding affinity to galectin-3 and galectin-8N.

As the sequences of galectin molecules used in the present invention, the conventionally known sequences (Barondes, S. H. et al., Cell, 76, 597-598 (1994)) can be used. In addition, the galectin molecules may have a mutation of amino acid, so long as the affinity of these galectin molecules for carbohydrates is not spoiled.

The galectin molecules used in the present invention can be produced using the generally used genetic engineering and biochemical techniques. In addition, conventionally known peptide synthesis methods, for example, chemical synthesis methods such as a liquid phase synthesis and a solid phase synthesis can be used in preparing the protein of the present invention.

Based on the above-described binding property between glycosaminoglycan molecules and galectin molecules, the present invention provides a complex between a galectin molecule and a glycosaminoglycan molecule which is capable of binding with the galectin molecule. The present invention also provides a carrier on which the galectin molecule constituting the complex is immobilized, for use in the separation, purification and/or detection of a glycosaminoglycan molecule constituting the galectin-glycosaminoglycan complex. In addition, the present invention provides a carrier on which the glycosaminoglycan molecule constituting the complex is immobilized, for use in the separation, purification and/or detection of a galectin molecule constituting the galectin-glycosaminoglycan complex.

Immobilization of the galectin molecule or glycosaminoglycan molecule onto a carrier is carried out typically by immobilizing a recombinant polypeptide with a water-insoluble carrier. Examples of the immobilization method include (1) a carrier binding method, (2) an inclusion method and the like and a composite method as a combination thereof. The methods generally used in the field can be used for the immobilization.

As the above-described carrier binding method, it can be carried out, for example, by a method using ionic interaction, hydrophobic interaction, physical adsorption or the like or a chemical bond such as a covalent bond.

In the above-described carrier binding method using ionic interaction, the carrier includes ion exchangers of polysaccharides such as dextran, cellulose, agarose and starch, for example, derivatives having a DEAE group, a TEAE group, a CM group, an alkylsulfonate group or the like, ion exchange resins and the like.

In the above-described carrier binding method using hydrophobic interaction, the carrier includes polystyrene beads and glass beads, as well as general carriers to which hydrophobic functional groups such as butyl group or phenyl group are bound, and the like.

In the above-described carrier binding method using physical adsorption, the carrier includes inorganic materials such as activated carbon, acid clay, bleached clay, kaolinite, alumina, silica gel, bentonite, metal oxides, hydroxyapatite and calcium phosphate, natural polymers such as starch, chitin, gluten, cellulose, agarose and tannin, synthetic polymers such as polystyrene, agarose derivatives having hydrophobic groups and the like.

The above-described carrier binding method using a chemical bond such as a covalent bond includes a peptide method, a diazo method, an alkylation method, a cyanogen bromide activation method, a binding method using a crosslinking agent, an immobilization method using Ugi reaction, an immobilization method using thiol-disulfide exchange reaction, a Schiff base forming method, a chelate binding method, a tosyl chloride method, a biochemical specific binding method and the like. Preferably, in the case of a more stable bond such as a covalent bond, the method can be carried out by using a reaction of a thiol group with a maleimido group, a reaction of a pyridyl disulfide group with a thiol group, a reaction of an amino group with an aldehyde group and the like, and a method can be applied thereto by optionally selecting it from conventionally known methods or the methods which can be easily carried out by those skilled in the art, as well as modified methods thereof. Preferably, substance which can form more stable binding such as a covalent bond, for example, a chemical binding agent or a crosslinking agent, is used.

The above-described chemical binding agent or crosslinking agent includes carbodiimide, isocyanate, a diazo compound, benzoquinone, aldehyde, periodic acid, a maleimide compound, a pyridyl disulfide compound and the like. Examples of the desirable agents include formaldehyde, glutaraldehyde, hexamethylene diisocyanate, hexamethylene diisothiocyanate, N,N'-polymethylenebisiodoacetamide, N,N'-ethylenebismaleimide, ethylene glycol bissuccinimidyl succinate, bisdiazobenzidine, 1-ethyl-3-(3-dimethylaminopropyl)carbodiimide, succinimidyl 3-(2-pyridyldithio)propionate (SPDP), N-succinimidyl 4-(N-maleimidomethyl)cyclohexane-1-carboxylate (SMCC), N-sulfosuccinimidyl 4-(N-maleimidomethyl)cyclohexane-1-carboxylate, N-succinimidyl (4-iodoacetyl)aminobenzoate, N-succinimidyl 4-(1-maleuimidophenyl)butyrate, N-($\epsilon$-maleimidocaproyloxy)succinimide (EMCS), iminothiolan, S-acetylmercaptosuccinic acid anhydride, methyl-3-(4'-dithiopyridyl)propione imidate, methyl-4-mercaptobutyryl imidate, methyl-3-mercaptopropione imidate, N-succinimidyl-5-acetyl mercaptoacetate and the like.

In the above-described peptide method, the immobilization is carried out by forming a peptide bond between a carrier and a desired polypeptide. For example, a carrier having a carboxyl group is made into a derivative of an azide, chloride, isocyanate or the like, and a peptide bond is formed between this and free amino group in the polypeptide. A reagent which is used in the peptide synthesis, for example, a carbodiimide reagent, Woodward reagent (N-ethyl-5-phenylisoxazolium-3'-sulfonate) or the like, is used. The peptide bond can also be formed between an amino group and a carboxyl group of the carrier and an amino group and a carboxyl group of the desired polypeptide.

The above-described diazo method is a method in which a carrier having an aromatic amino group is regarded as a diazonium compound, and this and a desired polypeptide are subjected to diazo coupling for immobilization. This can be suitably applied to the polypeptide which has a free amino group, an imidazolyl group of histidine, a phenolic hydroxyl group of tyrosine and the like. Examples of the carrier include a polysaccharide, an amino acid copolymer, a polyacrylamide, a styrene system resin, an ethylene-maleic acid copolymer, a porous glass-aromatic amino derivative and the like.

The above-described alkylation method is a method in which a free amino group, a phenolic hydroxyl group and a sulfhydryl group in the polypeptide are immobilized through their alkylation by a carrier having a reactive functional group such as a halogen. The carrier includes a halogenated acetyl derivative, a triazinyl derivative, a halogenated methacryl derivative and the like.

The above-described cyanogen bromide activation method is a method in which dextran, cellulose, agarose, starch or the like polysaccharide, porous glass or the like is activated with cyanogen bromide, and then the polypeptide is immobilized thereon. Among the binding methods which use crosslinking reagents, particularly when glutaraldehyde or the like bifunctional reagent is used, examples include aminosilane derivatives and the like of natural polymer, synthetic polymer, porous glass, porous ceramics and the like into which cellulose, agarose, albumin, gelatin, chitosan and the like are introduced, or which are possessed of the same.

The above-described Ugi reaction uses a condensation reaction which is occurred when the reaction is carried out in the coexistence of carboxyl group, amino group, aldehyde group or isonitrile group. In an example thereof, the reaction is carried out by adding acetaldehyde and 3-dimethylaminopropylisocyamide to a mixture of a carrier having a carboxyl group or an amino group with the polypeptide. The carrier includes a polysaccharide, an amino derivative of polyacrylamide, an isonitrile derivative of nylon and the like.

In the above-described biochemical specific binding method, a biochemical specific binding reaction between specific binding reaction pairs is used, and examples include an antigen and its antibody, an antibody and a hapten, an effector and a receptor, an enzyme and an enzyme inhibitor, enzyme substrates, coenzymes, prosthetic groups in conjugated protein, lectin and a carbohydrate-containing substance, an enzyme and an enzyme substrate, a nucleic acid and its complementary nucleic acid and the like which may be selected from conventionally known substances.

The above-described inclusion method is roughly divided into a method using a polymer gel prepared by entrapping the polypeptide in fine gel matrixes of a natural polymer or a synthetic polymer, such as a polysaccharide or a protein, and a method in which the polypeptide is entrapped in a space divided with a membrane. The membrane inclusion method includes a microcapsule type membrane inclusion method in which the polypeptide is wrapped in a translucent solid membrane, a method in which it is wrapped in a space created by a translucent hollow fiber or ultrafiltration membrane, a liposome type method in which it is wrapped in a liquid membrane and the like.

In the above-described method using a high molecular gel, the polypeptide is immobilized by entrapping it in matrixes of the high molecular gel having a network structure, so that the gel can be freely formed into a spherical form, a film form, a tubular form or a film form at the time of its immobilization. The preparation method of the gel includes a method in which the high molecular gel is formed by polymerizing a monomer and a crosslinking agent, a method in which a prepolymer or an oligomer is polymerized, a method in which the gel is formed by changing the polymer from a soluble state to insoluble state and the like. The polymer includes synthetic polymers such as polyacrylamide, polyvinyl alcohol, light-curable resin and urethane polymer, natural polymers such as κ-carrageenan, alginic acid, pectin, chitosan, starch and collagen, and the like.

When the above-described polyacrylamide is used, its gelation can be carried out using an acrylamide monomer, a crosslinking agent N,N'-methylenebisacrylamide, a polymerization accelerating agent N,N,N',N'-tetramethylethylenediamine, or a polymerization initiator potassium persulfate, or using radiation such as γ rays or X rays. When calcium alginate is used, it is used based on the fact that sodium alginate is soluble in water, but its calcium salt and aluminum salt are insoluble in water. A sodium alginate aqueous solution and the polypeptide are firstly mixed, and then the mixture is allowed to contact with an aqueous calcium chloride solution.

When κ-carrageenan is used, κ-carrageenan dissolves in water when heated but is gelatinized when an ammonium ion, a potassium ion, a calcium ion, an aliphatic amine or the like is present, so that the gel obtained in this manner is stabilized by crosslinking it with glutaraldehyde, hexamethylenediamine or the like.

When the above-described light-curable resin is used, a prepolymer prepared by using polyethylene glycol (PEG) or polypropylene glycol (PPG) having an appropriate polymerization degree as the principal chain and integrating a photosensitive group such as an acryloyl group, a methacryloyl group or a cinnamoyl group into its terminal can be used. Said prepolymer can be gelatinized by mixing with a solution containing the polypeptide in the presence of a photosensitizer benzoin ethyl ether or benzoin isobutyl ether, and then irradiating ultraviolet rays thereto. A urethane polymer can be gelatinized by merely mixing it with an aqueous solution containing the polypeptide.

In the above-described microcapsule type membrane inclusion method, capsules are formed by coating and immobilizing the polypeptide, for example, when a hydrophilic monomer and a hydrophobic monomer are polymerized at the interface, or by a submerged drying method in which the polymer is dissolved in an organic solvent having high volatility, such as benzene, hexane or chloroform, an aqueous solution containing the polypeptide is dispersed therein to make a primary emulsion, this primary emulsion is then dispersed in an aqueous solution containing a protective colloidal substance such as gelatin, polyvinyl alcohol or a surfactant, and then the organic solvent is removed from the thus obtained secondary emulsion.

According to the above-described method in which the polypeptide is immobilized onto a hollow fiber or ultrafiltration membrane, it is possible to immobilize two or more of the polypeptides and further to immobilize them in the free state without binding to the membrane.

The useful references include, for example, certain references [U.S. Pat. No. 4,003,988; B. K. Van Weemen and A. H. A. Schuurs, *FEBS Letters*, 15(15), 232-235 (1971); P. Leinikki; Suvi Passila, *J. Clin. Path.*, 29, 116-120 (1976); B. R. Brodeur, F. E. Ashton and B. B. Diena, *The Journal of Medical Microbiology*, 15(1), 1-9 (1981); *J. Clin. Path.*, 29, 150-153 (1976); *Enzyme Immunoassay*, edited by Eiji Ishikawa et al., published by Igaku Shoin (1978)] and the like.

The above-described water-insoluble carrier means a carrier which is substantially insoluble in liquid media to be used in the immobilization, preservation, measurement and the like. As the carrier, various substances which are used in the specific binding reactions are known, and a carrier selected from these conventionally known substances can also be used in the present invention. The carrier which can be particularly preferably used includes those which are comprising organic high molecular substances such as the organic high molecular substances obtained by emulsifying and polymerizing cross-linked albumin, collagen, gelatin, agarose, cross-linked agarose, cellulose, microcrystalline cellulose, carboxymethylcellulose, cellulose acetate, cross-linked dextran, polyacrylamide, cross-linked polyacrylamide, polyethylene, polypropylene, polyvinyl chloride, polyvinyl acetate, polyacrylamide, polyesters such as polymethacrylate, polystyrene, a styrene-butadiene copolymer, a styrene-methacrylate copolymer, a polyglycidyl methacrylate and acrolein-ethylene glycol dimethacrylate copolymer, polyamide such as nylon, polyurethane, polyepoxy resin and the like, and of inorganic materials glass such as activated glass, silica gel, alumina and the like, into which a functional group is introduced by a silane coupling agent or the like, if necessary.

When a carrier on which the galectin molecule that constitutes the galectin-glycosaminoglycan complex of the present invention is packed in a column or the like, and a sample to be tested is passed through the column, it can be used in the separation, purification and/or detection of the complex or the glycosaminoglycan molecule constituting the complex. In addition, when a carrier on which the galectin molecule that constitutes the galectin-glycosaminoglycan complex of the present invention is packed in a column or the like, and a sample to be tested is passed through the column, it can be used in the purification, separation and/or detection of the complex or the galectin molecule constituting the complex.

The above-described sample to be tested includes a glycoprotein, a glycopeptide, a glycolipid, a carbohydrate-containing non-peptide compound, a synthetic compound, a fermentation product, a plant extract, a tissue extract of an animal or the like, a cell extract and the like. A galectin inhibitor or a compound having the activity to inhibit galectin, particularly a synthetic compound, may be included in the test compound to be used in the sample to be tested. These compounds may be novel compounds or conventionally known compounds.

It is preferable that detection of the glycosaminoglycan molecule bound to the above-described galectin molecule-immobilized carrier via the galectin molecule or of the formed galectin-glycosaminoglycan complex is carried out using a substance which specifically binds to the glycosaminoglycan. It is also preferably that detection of the galectin molecule bound to the above-described glycosaminoglycan-immobilized carrier via the glycosaminoglycan molecule or of the formed galectin-glycosaminoglycan complex is carried out using a substance which specifically binds to the galectin molecule. As the substances, for example, antibodies for the glycosaminoglycan molecule or galectin molecule are desirable in view of the strong affinity.

As the above-described antibodies, polyclonal antibodies or monoclonal antibodies can be used with no particular limitation. When the above-described antibody for glycosaminoglycan molecule or galectin molecule is used in the above-described detection, it is desirable to label the antibody a secondary antibody for the antibody with a labeling substance, because it renders possible more accurate detection of the glycosaminoglycan molecule or galectin molecule.

The above-described labeling substance includes either one part of a specific binding pair (e.g., avidin such as biotin or streptoavidin, lectin, a carbohydrate which is recognized by the lectin, or the like); a fluorescent material such as FITC, Phycoerythrin, europium, phycocyanin, Rhodamine, Texas Red, umbelliferone, tricolor, cyanin, or 7-amino-4-methyl-coumarin-3-acetic acid (AMCA); a luminescent material such as luminol, acridinium or lucigenin; an enzyme such as alkaline phosphatase, β-galactosidase, peroxidase or glucose oxidase; a hapten such as dinitrofluorobenzene, AMP (adenosine monophosphate) or 2,4-dinitroaniline; a radioisotope such as $^{125}$I, $^{131}$I, and $^{3}$H; and the like.

The above-described labeling substance can be detected by a generally used method suited for the labeling substance to be used. For example, when a peroxidase classified into the above-described enzyme is used as the labeling substance, it is possible to detect it based on the coloring of solution by reacting an oxygen acceptor such as tetramethylbenzidine (TMB) with an oxygen donor such as hydrogen peroxide ($H_2O_2$).

The present invention provides a kit for use in the purification, separation and/or detection of the galectin-glycosaminoglycan complex concerned in the present invention or the galectin molecule constituting the complex, which comprises a carrier on which the glycosaminoglycan molecule constituting the complex is immobilized. The present invention also provides a kit for use in the separation, purification and/or detection of the galectin-glycosaminoglycan complex concerned in the present invention or the glycosaminoglycan molecule constituting the complex, which comprises a carrier on which the galectin molecule constituting the complex is immobilized.

It is considered that galectin molecules are exerting various physiological functions in the living body by binding to β-galactoside-containing carbohydrates. Based on this, functions of galectin molecules can be enhanced or inhibited by the glycosaminoglycan molecules applied from the outside. Accordingly, the present invention provides a method for enhancing or inhibiting biological activity of the galectin molecule constituting the galectin-glycosaminoglycan complex concerned in the present invention, which comprises using the complex. The present invention also provides a composition for enhancing or inhibiting biological activity of the galectin molecule constituting the galectin-glycosaminoglycan complex concerned in the present invention, which comprises the glycosaminoglycan molecule constituting the complex. It is also possible to use the composition and the galectin-glycosaminoglycan complex concerned in the present invention as various medical materials for preventing and/or treating various diseases.

The present invention is further described below in detail based on Examples.

EXAMPLE 1

Preparation of Various Galectin Molecules-immobilized Columns:

Respective galectin molecules were prepared by conventionally known methods, at National Institute of Advanced Industrial Science and Technology (plasmids for galectin-1, 8N, 8C, 9N and 9C were obtained from Kagawa University, and a plasmid for galectin-3 from Teikyo University, and expression and purification of the proteins were carried out in accordance with the usual methods).

Various galectin molecules-immobilized columns were prepared by the method described by Nakamura S, Yagi F, Totani K, Ito γ and Hirabayashi J in *FEBS J.*, 272, 2784-2799 (2005), using NHS Sepharose (manufactured by Amersham Bioscience) as the carrier for immobilizing galectin molecules and in accordance with the instructions attached thereto (put in parentheses is immobilization concentration, mg galectin/ml carrier).

Each galectin molecule was immobilized onto the carrier at the following concentration; galectin-1 (0.8 mg/ml), galectin-3 (0.5 mg/ml), galectin-8N (3.6 mg/ml), galectin-8C (4.0 mg/ml), galectin-9N (3.6 mg/ml), galectin-9C (3.0 mg/ml). The carrier on which each galectin was immobilized was charged into a stainless steel miniature column (2 mm in inner diameter, 10 mm in length; manufactured by Shimadzu Corp.).

EXAMPLE 2

Preparation of Fluorescence-labeled (Pyridylamination) Glycosaminoglycan Molecule:

Chondroitin (CH), chondroitin sulfate A (CSA), dermatan sulfate (CSB), chondroitin sulfate C(CSC), chondroitin sulfate D (CSD), chondroitin sulfate E (CSE) and cornea type keratan sulfate (KS-I) were purchased from Seikagaku Corporation.

Hyaluronan (HA), N-acetylheparosan (NAH) and cartilage type keratan sulfate (KS-II) were respectively prepared from a cockscomb, an *Escherichia coli* K5 culture supernatant and a shark cartilage at Seikagaku Corporation. Dermatan (DN) was prepared by carrying out complete de-sulfation of CSB by a conventionally known chemical technique.

Each of G2K1, G1L1, G4L4, L2L2, L2L4, L4L4 and SL2L4 as keratan sulfate-constituting oligosaccharides was prepared by the method described in JP-A-2006-047240.

Fluorescence labeling of each of the above-described carbohydrates was carried out by the broadly known pyridylamination method [Hase S, Ikenaka T and Matsushima Y, *Biochem. Biophys. Res. Commun.*, 85, 257-263 (1978)], and the product was purified by a conventionally known gel filtration HPLC method. On the other hand, regarding the chondroitin oligosaccharides (CH3 to CH12), those which were prepared by the method described in PCT/JP2006/322847 were used.

EXAMPLE 3

FAC Example (1): Affinity Test

A high performance liquid chromatography (HPLC) system was equipped with a galectin molecule-immobilized column, and the test was carried out by the method described in Nakamura S, Yagi F, Totani K, Ito γ and Hirabayashi J in *FEBS J.*, 272, 2784-2799 (2005).

Injection volume of samples (pyridyl-aminated glycosaminoglycan and a negative control sample: a pyridyl-aminated sugar which does not interact with galectin) was set to 500 μl, and amount of the total sample to approximately from 5 to 50 pmol.

As the negative control sample, pyridyl-aminated N-acetylglucosamine (PA-GlcNAc, manufactured by Takara Bio, pyridyl-aminated glycosaminoglycan-oligosaccharide sample control) or pyridyl-aminated pullulan (prepared by carrying out pyridylamination of standard pullulan manufactured by Shodex, pyridyl-aminated glycosaminoglycan polysaccharide sample control) was used, and a V–V₀ value was calculated from their eluate volume (V₀ value) measured by fluorescence detection and the eluate volume (V value) of the sample, namely pyridyl-aminated glycosaminoglycan carbohydrate, and this was used as the index of interaction strength (*Protein, Nucleic Acid and Enzyme*, 48(8), 1206-1212 (2003)). Results of the example (1) are shown in Table 3.

As shown in Table 3, the following results were obtained.

(1) Gallectin-8C did not bind to the tested glycosaminoglycan molecules.

(2) KS-I bound to galectin-1, 3, 9N and 9C. KS-II bound to galectin-3, 9N and 9C, but weaker than their binding with KS-I. This was considered to be due to the fact that many of the galactose molecules possessed by KS-I do not have the sulfate group, while most of the galactose molecules possessed by KS-II have the sulfate group [Funderburgh J. L., *Glycobiology*, 951 (2000)].

(3) Among the keratan sulfate-constituting oligosaccharides, oligosaccharides which are possessed of galactose with sulfate group (namely G2K1, G1L1, L2L2, L2L4 and SL2L4) bound to various galectin molecules. On the other hand, oligosaccharides in which all of their galactose molecules with sulfate group (namely G4L4 and L4L4) did not bind to the tested galectin molecules.

(4) HA, NAH and chondroitin sulfates (CSA, CSB, CSC, CSD and CSE) did not bind to the tested galectin molecules.

TABLE 3

| $V - V_0$ Value (μl) | Galectin-1 (0.8 mg/ml) | Galectin-3 (0.5 mg/ml) | Galectin-8N (3.6 mg/ml) | Galectin-8C (4.0 mg/ml) | Galectin-9N (3.6 mg/ml) | Galectin-9C (3.0 mg/ml) |
|---|---|---|---|---|---|---|
| HA    | <5.0       | <5.0       | <5.0       | <5.0 | <5.0         | <5.0       |
| CH    | <5.0       | 19.2 ± 2.2 | <5.0       | <5.0 | 171.4 ± 19.0 | <5.0       |
| DN    | <5.0       | 33.4 ± 3.7 | 8.3 ± 0.9  | <5.0 | 175.1 ± 28.7 | <5.0       |
| NAH   | <5.0       | <5.0       | <5.0       | <5.0 | <5.0         | <5.0       |
| CSA   | <5.0       | <5.0       | <5.0       | <5.0 | <5.0         | <5.0       |
| CSB   | <5.0       | <5.0       | <5.0       | <5.0 | <5.0         | <5.0       |
| CSC   | <5.0       | <5.0       | <5.0       | <5.0 | <5.0         | <5.0       |
| CSD   | <5.0       | <5.0       | <5.0       | <5.0 | <5.0         | <5.0       |
| CSE   | <5.0       | <5.0       | <5.0       | <5.0 | <5.0         | <5.0       |
| KS-I  | 10.3 ± 4.5 | 21.7 ± 4.3 | <5.0       | <5.0 | 105.3 ± 22.6 | 12.2 ± 1.0 |
| KS-II | <5.0       | 10.1 ± 1.1 | <5.0       | <5.0 | 10.4 ± 0.3   | 6.4 ± 1.0  |
| G2K1  | 21.8 ± 1.9 | 11.6 ± 0.1 | <5.0       | <5.0 | 5.1 ± 1.3    | 6.7 ± 0.2  |
| G1L1  | <5.0       | 14.2 ± 1.3 | <5.0       | <5.0 | 13.6 ± 0.5   | <5.0       |
| G4L4  | <5.0       | <5.0       | <5.0       | <5.0 | <5.0         | <5.0       |
| L2L2  | 6.2 ± 1.7  | 22.6 ± 1.1 | <5.0       | <5.0 | 8.8 ± 0.3    | 7.7 ± 0.4  |
| L2L4  | 5.8 ± 0.2  | 15.8 ± 1.8 | <5.0       | <5.0 | 6.6 ± 1.4    | 5.3 ± 0.7  |
| L4L4  | <5.0       | <5.0       | <5.0       | <5.0 | <5.0         | <5.0       |
| SL2L4 | <5.0       | 8.2 ± 0.2  | 26.5 ± 0.9 | <5.0 | <5.0         | <5.0       |
| CH3   | <5.0       | <5.0       |            |      | 49.6 ± 8.2   |            |
| CH4   | <5.0       | <5.0       |            |      | 45.3 ± 4.8   |            |
| CH5   | <5.0       | <5.0       |            |      | 45.6 ± 4.6   |            |
| CH6   | <5.0       | 5.8 ± 1.4  |            |      | 33.3 ± 3.0   | <5.0       |
| CH7   | <5.0       | 10.7 ± 1.9 |            |      | 146.4        | <5.0       |
| CH8   | <5.0       | 7.8 ± 1.9  |            |      | 116.2        | <5.0       |
| CH9   | <5.0       | 15.6 ± 2.5 |            |      | 199.4        | <5.0       |
| CH10  | <5.0       | 11.8 ± 3.3 |            |      | 171.5        | <5.0       |
| CH11  |            | 21.4 ± 4.2 |            |      | 218.8        |            |
| CH12  |            | 16.8 ± 2.1 |            |      | 196.0        |            |

V–V₀ values of pyridyl-aminated glycosaminoglycans (HA, CH, DN, NAH, CSA, CSB, CSC, CSD, CSE, KS-I and KS-II) were calculated based on PA-GlcNAc, and V–V₀ values of pyridyl-aminated glycosaminoglycan-oligosaccharides (G2K1, G1L1, G4L4, L2L2, L2L4, L4L4, SL2L4 and CH3 to CH12) based on pyridyl-aminated pullulan, respectively.

In this connection, when the calculated value of the V–V₀ value was less than 5 μl, it was regarded as less than the interaction detection limit in this example. That is, it is shown in Table 3 that interaction (binding) was found between galectin-glycosaminoglycan carbohydrate which showed a V–V₀ value of 5 μl or more.

(5) It was found that galectin-3 and 9N bind to CH and DN and also bind to chondroitin oligosaccharide chains (CH3 to CH12). Although CH and CH oligosaccharides do not have galactose in their structures, they are possessed of N-acetylgalactosamine, so that it was considered that the binding is carried out via the latter.

EXAMPLE 4

FAC Example (2): Competitive Inhibition Test

A model test on a competitive inhibition was carried out by FAC, in which binding of a galectin molecule with a carbohydrate which binds to the galectin molecule is inhibited by a glycosaminoglycan molecule. The FAC was carried out in accordance with the above-described example (1). In addition, as a model carbohydrate which is known to be bound to the galectin molecule, a pyridylamination product of lacto-N-neotetraose (LNnT hereinafter, Gal β1-4 GlcNAc β1-3 Gal β1-4 Glc, purchased from Seikagaku Corporation) was used.

In the test, 5.0 nM in final concentration of PA-LNnT sample solution was mixed with various concentration of glycosaminoglycan molecule (not pyridyl-aminated, namely an inhibitory carbohydrate) to measure the eluate volume ($V_2$ value) by FAC, and the inhibition ratio (%) was calculated as follows from the eluate volume ($V_1$ value) before the mixing and the eluate volume ($V_0$ value) of a negative control sample.

$$\text{Inhibition ratio (\%)} = 100 \times (V_1 - V_2)/(V_1 - V_0) \quad \text{Formula 1}$$

In this connection, the unlabeled (not pyridyl-aminated) CH4, CH6, CH10, HA4 and CSA4 were respectively prepared at Seikagaku Corporation in accordance with a conventionally known method. Results of the FAC example (2) are shown in Tables 4 and 5.

TABLE 4

Inhibition test for the binding of galectin-3 with LNnT

| Compound | Final conc. | $V_2 - V_0$ (μl) | $V_1 - V_0$ (μl) | Inhibition ratio (%) |
|---|---|---|---|---|
| CH4 | 10 μM | 26.7 | 30.6 | 12.7 |
| CH4 | 50 μM | 20.8 | 30.6 | 32.0 |
| CH4 | 250 μM | 15.9 | 30.6 | 48.0 |
| CH6 | 10 μM | 29.0 | 30.6 | 5.2 |
| CH10 | 10 μM | 18.9 | 30.6 | 38.2 |
| HA4 | 10 μM | 31.4 | 30.6 | 0.0 |
| HA4 | 50 μM | 31.8 | 30.6 | 0.0 |
| CSA4 | 10 μM | 31.3 | 30.6 | 0.0 |

TABLE 5

Inhibition test for the binding of galectin-9N with LNnT

| Compound | Final conc. | $V_2 - V_0$ (μl) | $V_1 - V_0$ (μl) | Inhibition ratio (%) |
|---|---|---|---|---|
| CH4 | 1 μM | 16.9 | 20.3 | 16.7 |
| CH4 | 5 μM | 15.0 | 20.3 | 26.1 |
| CH4 | 10 μM | 13.7 | 20.3 | 32.5 |
| CH4 | 50 μM | 5.8 | 20.3 | 71.4 |

As shown in Table 4, binding of galectin-3 with LNnT was not inhibited by CSA4 and HA4, but their inhibitory effects were confirmed in the case of the chondroitin oligosaccharide bound to galectin-3 in the FAC example (1). In addition, as shown in Table 5, it was confirmed that binding of galectin-9N with LNnT is inhibited by CH4 concentration-dependently.

As has been described in the foregoing, galectin-glycosaminoglycan complexes are provided by the present invention as novel substances, and tools for separating, purifying and detecting galectin molecules or glycosaminoglycan molecules are also provided. Also, since there is a possibility that a galectin molecule-binding glycosaminoglycan molecule can be applied to the control of the galectin molecule in the living body, its application to medical treatment is expected.

In addition, the affinity between various galectin molecules and glycosaminoglycan molecules revealed by the present invention can be applied to the method for estimating structure of glycosaminoglycan carbohydrate described for example in International Publication WO 2005/064327.

While the invention has been described in detail and with reference to specific embodiments thereof, it will be apparent to one skill in the art that various changes and modifications can be made therein without departing from the spirit and scope thereof.

This application is based on Japanese application No. 2006-140600 filed on May 19, 2006, the entire contents of which are incorporated hereinto by reference. All references cited herein are incorporated in their entirety.

What is claimed is:

1. An isolated complex consisting of a galectin-3 multimer and a chondroitin oligosaccharide chain having any one of the structures represented by the following formula (6) to (12):

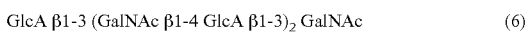
GlcA β1-3 (GalNAc β1-4 GlcA β1-3)$_2$ GalNAc            (6)

(GalNAc β1-4 GlcA β1-3)$_3$ GalNAc                      (7)

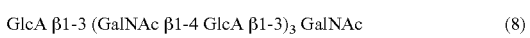
GlcA β1-3 (GalNAc β1-4 GlcA β1-3)$_3$ GalNAc            (8)

(GalNAc β1-4 GlcA β1-3)$_4$ GalNAc                      (9)

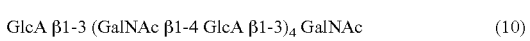
GlcA β1-3 (GalNAc β1-4 GlcA β1-3)$_4$ GalNAc           (10)

(GalNAc β1-4 GlcA β1-3)$_5$ GalNAc                     (11)

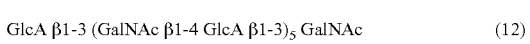
GlcA β1-3 (GalNAc β1-4 GlcA β1-3)$_5$ GalNAc           (12)

wherein GlcNAc represents an N-acetylglucosamine residue, GalNAc represents an N-acetylgalactosamine residue, GlcA represents a glucuronic acid residue, β1-4 represents a β1-4 glycosidic linkage, and β1-3 represents a β1-3 glycosidic linkage.

2. A composition comprising the complex according to claim 1 and a carrier.

3. A method for separating and/or purifying the chondrotin oligosachharide chain having any one of the structures represented by the formula (6) to (12) set forth in claim 1 in a sample comprising brining the sample to be tested into contact with the complex of claim 1 which is immobilized on a carrier, and separating said chondroitin oligosaccharide chain from the immobilized complex.

4. A method of detecting the chondroitin oligosaccharide chain having any one of the structures represented by the formula (6) to (12) set forth in claim 1 in a sample comprising immobilizing the complex of claim 1 on a carrier, contacting the immobilized complex with said sample, and assaying for binding of the chondroitin oligosaccharide on said carrier.

* * * * *